(12) United States Patent
Andersch et al.

(10) Patent No.: US 6,686,387 B2
(45) Date of Patent: Feb. 3, 2004

(54) SYNERGISTIC INSECTICIDAL MIXTURES

(75) Inventors: Wolfram Andersch, Bergisch Gladbach (DE); Hans-Jürgen Schnorbach, Monheim (DE); Detlef Wollweber, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/196,873

(22) Filed: Jul. 17, 2002

(65) Prior Publication Data

US 2003/0092641 A1 May 15, 2003

Related U.S. Application Data

(62) Division of application No. 09/700,675, filed as application No. PCT/EP99/03394 on May 17, 1999, now Pat. No. 6,444,667.

(30) Foreign Application Priority Data

May 26, 1998 (DE) .......................... 198 23 396

(51) Int. Cl.[7] ................. A61K 31/335; A61K 31/33
(52) U.S. Cl. ..................... 514/450; 514/183
(58) Field of Search .................. 514/241, 256, 514/341, 357, 183, 450

(56) References Cited

U.S. PATENT DOCUMENTS 6,001,981 A * 12/1999 DeAmics et al. ............ 536/7.1

FOREIGN PATENT DOCUMENTS

EP 677247 * 10/1995

OTHER PUBLICATIONS

Database Cropu Online! STN–International, STN–accession No. 1997–84126, R.M. Duchesne et al.: "Efficacite de spinosad a differentes concentrations contre le doryphore de la pomme de terre, saison 1996", XP002114424 abstract, & Pest Manage. Res. Rep., 1996, p. 31.

Chemical Abstracts, vol. 127, No. 9, Sep. 1, 1997, Columbus, Ohio, US; abstract No. 118585, D.R. Johnson et al.: "Comparison of new insecticide for the control of bollworm (*Helicoverpa zea*) and tobacco budworm (*Heliothis virescens*) in Arkansas" XP002114422 abstract & Proc.—Beltwide Cotton Conf., vol. 2, 1997, pp. 947–949.

Database Cropu Online! STN–International, STN–accession No. 98–88801 C.E. Sorenson et al, "Control of tobacco aphids with systemic insecticides, 1997B" XP002114423 abstract & Arthropod Manage, Tests, vol. 23, 1998, p. 302.

* cited by examiner

Primary Examiner—Alton N. Pryor
(74) Attorney, Agent, or Firm—Richard E.L. Henderson; John E. Mrozinski, Jr.

(57) ABSTRACT

The invention relates to insecticidal mixtures of spinosyns and agonists or antagonists of nicotinic acetylcholine receptors for protecting plants against attack by pests.

4 Claims, No Drawings

SYNERGISTIC INSECTICIDAL MIXTURES

This application is a divisional of U.S. Ser. No. 09/700,675 filed on Nov. 17, 2000 now U.S. Pat. No. 6,444,667 which a PCT/EP99/03394 filed May 17, 1999.

FIELD OF THE INVENTION

The invention relates to synergistic insecticidal mixtures of one or more spinosyns and agonists or antagonists of nicotinic acetylcholine receptors and to their use for controlling animal pests.

BACKGROUND OF THE INVENTION

It is already known that spinosyns can be used for controlling insects (WO 97/00265, WO 93/09126, WO 94/20518, U.S. Pat. No. 5,362,634, No. 5,202,242, No. 5,670,364, No. 5,227,295, see also DowElanco trade magazine Down to Earth, Vol. 52, No. 1, 1997).

However, spinosyns on their own do not always exhibit satisfactory insecticidal activity.

Furthermore, it is known that agonists and antagonists of nicotinic acetylcholine receptors can be used for controlling insects.

DETAILED DESCRIPTION OF THE INVENTION

It has now been found that mixtures of spinosyns and at least one agonist or antagonist of acetylcholine receptors of the formula (III) are synergistically effective and suitable for controlling animal pests. Owing to this synergism, it is possible to employ considerably lower amounts of active compounds, i.e. the activity of the mixture is greater than the activity of the individual components.

The spinosyns are known compounds. The fermentation product (A 83543) described in U.S. Pat. No. 5,362,634 comprises various compounds which are referred to as spinosyn A, B, C etc. (cf. WO 97/00265, WO 93/09126 and WO 94/20518). The spinosyns can be represented by the formulae (I) and (II) below.

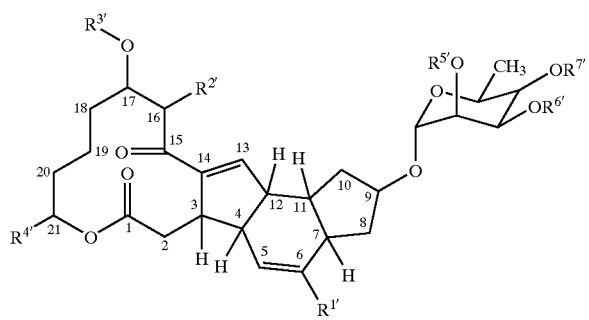

(I)

| Compound | $R^{1'}$ | $R^{2'}$ | $R^{3'}$ | $R^{4'}$ | $R^{5'}$ | $R^{6'}$ | $R^{7'}$ |
|---|---|---|---|---|---|---|---|
| spinosyn A | H | $CH_3$ | $(CH_3)_2N$—sugar—$CH_3$ | $C_2H_5$ | $CH_3$ | $CH_3$ | $CH_3$ |
| spinosyn B | H | $CH_3$ | $(CH_3)_2NH$—sugar—$CH_3$ | $C_2H_5$ | $CH_3$ | $CH_3$ | $CH_3$ |
| spinosyn C | H | $CH_3$ | $H_2N$—sugar—$CH_3$ | $C_2H_5$ | $CH_3$ | $CH_3$ | $CH_3$ |
| spinosyn D | $CH_3$ | $CH_3$ | $(CH_3)_2N$—sugar—$CH_3$ | $C_2H_5$ | $CH_3$ | $CH_3$ | $CH_3$ |
| spinosyn E | H | $CH_3$ | $(CH_3)_2N$—sugar—$CH_3$ | $CH_3$ | $CH_3$ | $CH_3$ | $CH_3$ |

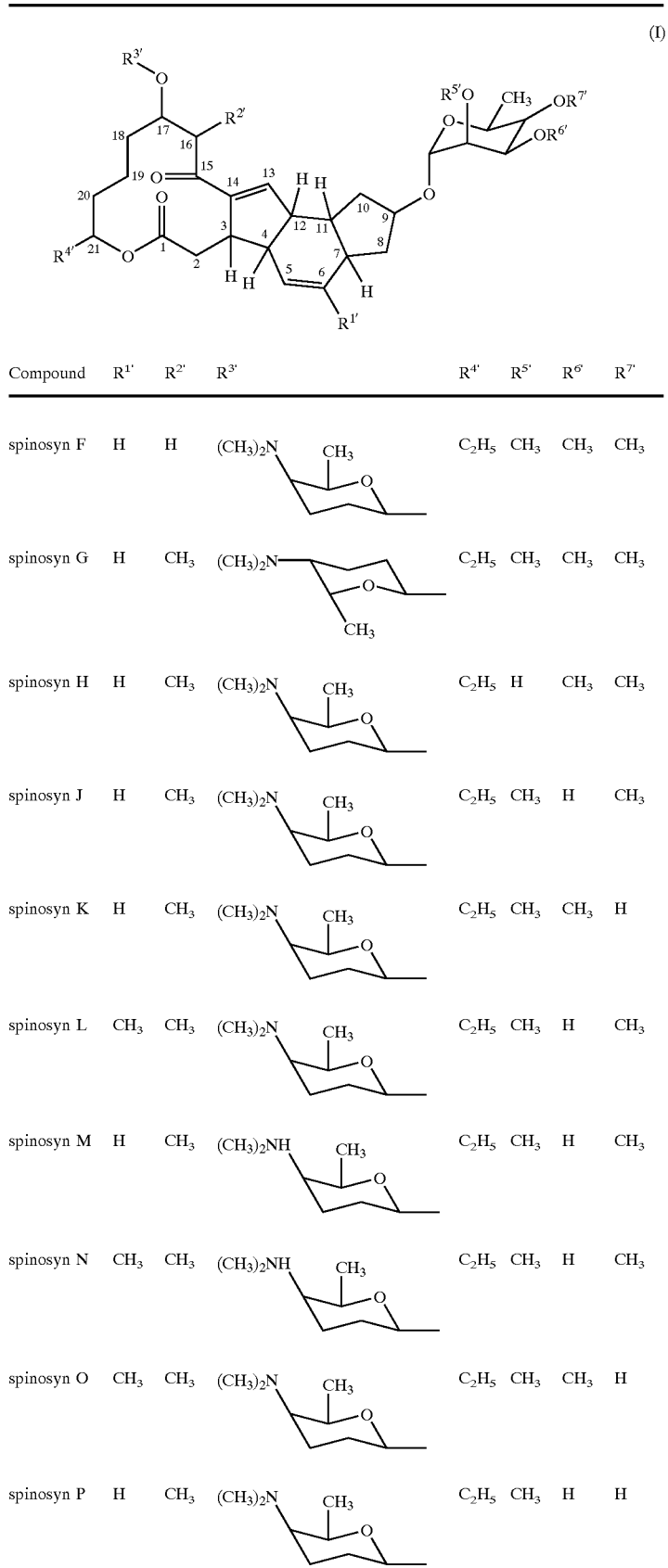

(I)

| Compound | R¹' | R²' | R³' | R⁴' | R⁵' | R⁶' | R⁷' |
|---|---|---|---|---|---|---|---|
| spinosyn F | H | H | (CH₃)₂N-sugar | $C_2H_5$ | $CH_3$ | $CH_3$ | $CH_3$ |
| spinosyn G | H | $CH_3$ | (CH₃)₂N-sugar | $C_2H_5$ | $CH_3$ | $CH_3$ | $CH_3$ |
| spinosyn H | H | $CH_3$ | (CH₃)₂N-sugar | $C_2H_5$ | H | $CH_3$ | $CH_3$ |
| spinosyn J | H | $CH_3$ | (CH₃)₂N-sugar | $C_2H_5$ | $CH_3$ | H | $CH_3$ |
| spinosyn K | H | $CH_3$ | (CH₃)₂N-sugar | $C_2H_5$ | $CH_3$ | $CH_3$ | H |
| spinosyn L | $CH_3$ | $CH_3$ | (CH₃)₂N-sugar | $C_2H_5$ | $CH_3$ | H | $CH_3$ |
| spinosyn M | H | $CH_3$ | (CH₃)₂NH-sugar | $C_2H_5$ | $CH_3$ | H | $CH_3$ |
| spinosyn N | $CH_3$ | $CH_3$ | (CH₃)₂NH-sugar | $C_2H_5$ | $CH_3$ | H | $CH_3$ |
| spinosyn O | $CH_3$ | $CH_3$ | (CH₃)₂N-sugar | $C_2H_5$ | $CH_3$ | $CH_3$ | H |
| spinosyn P | H | $CH_3$ | (CH₃)₂N-sugar | $C_2H_5$ | $CH_3$ | H | H |

-continued (I)

| Compound | R1' | R2' | R3' | R4' | R5' | R6' | R7' |
|---|---|---|---|---|---|---|---|
| spinosyn Q | CH₃ | CH₃ | (CH₃)₂N-sugar | C₂H₅ | H | CH₃ | CH₃ |
| spinosyn R | H | CH₃ | (CH₃)₂NH-sugar | C₂H₅ | H | CH₃ | CH₃ |
| spinosyn S | H | CH₃ | (CH₃)₂N-sugar | CH₃ | H | CH₃ | CH₃ |
| spinosyn T | H | CH₃ | (CH₃)₂N-sugar | C₂H₅ | H | H | CH₃ |
| spinosyn U | H | CH₃ | (CH₃)₂N-sugar | C₂H₅ | H | CH₃ | H |
| spinosyn V | CH₃ | CH₃ | (CH₃)₂N-sugar | C₂H₅ | H | CH₃ | H |
| spinosyn W | CH₃ | CH₃ | (CH₃)₂NH-sugar | C₂H₅ | CH₃ | H | H |
| spinosyn Y | H | CH₃ | (CH₃)₂N-sugar | C₂H₅ | CH₃ | CH₃ | H |
| spinosyn A 17-Psa | H | CH₃ | H | C₂H₅ | CH₃ | CH₃ | CH₃ |
| spinosyn D 17-Psa | CH₃ | CH₃ | H | C₂H₅ | CH₃ | CH₃ | CH₃ |
| spinosyn E 17-Psa | H | CH₃ | H | C₂H₅ | CH₃ | CH₃ | CH₃ |
| spinosyn F 17-Psa | H | H | H | C₂H₅ | CH₃ | CH₃ | CH₃ |
| spinosyn H 17-Psa | H | CH₃ | H | C₂H₅ | H | CH₃ | CH₃ |
| spinosyn J 17-Psa | H | CH₃ | H | C₂H₅ | CH₃ | H | CH₃ |
| spinosyn L 17-Psa | CH₃ | CH₃ | H | C₂H₅ | CH₃ | H | CH₃ | and

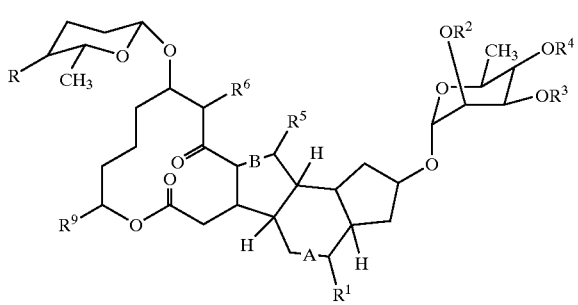

| Compound | R¹' | R²' | R³' | R⁵' | |
|---|---|---|---|---|---|
| spinosyn A 9-Psa | H | CH₃ | (CH₃)₂N-[sugar with CH₃, O] | C₂H₅ | H |
| spinosyn D 9-Psa | CH₃ | CH₃ | (CH₃)₂NH-[sugar with CH₃, O] | C₂H₅ | H |
| spinosyn A aglycone | H | CH₃ | H | C₂H₅ | H |
| spinosyn D aglycone | CH₃ | CH₃ | H | C₂H₅ | H |

Semisynthetic spinosyns of the formula (Ia)

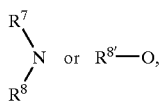

in which
A and B each represent a single bond, a double bond or an epoxide unit,
R represents

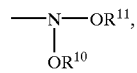

$R^1$ represents hydrogen or methyl,
$R^2$, $R^3$ and $R^4$ independently of one another each represent $C_1$–$C_4$-alkyl, $C_1$–$C_4$-halogenoalkyl, $C_1$–$C_4$-alkylcarbonyl or protected hydroxyl,
$R^5$ represents hydrogen, $C_1$–$C_4$-alkyl, $C_1$–$C_4$-alkylamino or represents alkylhydroxylamino of the formula $$-N-OR^{11},$$
$$\phantom{-N-}OR^{10}$$

in which
$R^{10}$ and $R^{11}$ independently of one another each represent hydrogen, $C_1$–$C_4$-alkyl or $C_1$–$C_5$-alkylcarbonyl,
$R^6$ represents hydrogen or methyl,
$R^7$, $R^8$ and $R^{8'}$ independently of one another each represent $C_1$–$C_4$-alkyl, $C_1$–$C_4$-halogenoalkyl or $C_1$–$C_4$-alkylcarbonyl or represent protected amino and
$R^9$ represents methyl or ethyl
are also known (WO 97/00265).

The compounds disclosed in WO 97/00265 are expressly incorporated into the present application by way of reference.

The mixtures according to the invention comprise at least one spinosyn of the formula (I), (Ia) or (II).

Preference is given to synergistic mixtures with at least one spinosyn of the formula (I) or (II).

Particular preference is given to synergistic mixtures which comprise a mixture of spinosyn A and spinosyn D, where the ratio of spinosyn A to spinosyn D is generally between approximately 80:20 and approximately 98:2, and where preference is given to a value of approximately 85:15.

Very particular preference is given to using Spinosad (see, for example, DowElanco trade magazine Down to Earth, vol. 52, No. 1, 1997 and literature cited therein) which essentially consists of a mixture of spinosyn A and spinosyn D in a ratio of approximately 85:15.

Use is made, in particular, of the fermentation product A 83543 known from U.S. Pat. No. 5,362,634 which comprises approximately 85 to 90% of spinosyn A, approximately 10 to 15% of spinosyn D and smaller amounts of the spinosyns B, C, E, F, G, H and J.

It is also possible to use the acid addition salts described therein.

The agonists and antagonists of the nicotinic acetylcholine receptors are known compounds which are known from the following publications:
European Published Specifications Nos. 464 830, 428 941, 425 978, 386 565, 383 091, 375 907, 364 844, 315 826, 259 738, 254 859, 235 725, 212 600, 192 060, 163 855, 154 178, 136 636, 136 686, 303 570, 302 833, 306 696, 189 972, 455 000, 135 956, 471 372, 302 389, 428 941, 376 279, 493 369, 580 553, 649 845, 685 477, 483 055, 580 553;
German Offenlegungsschriften Nos. 3 639 877, 3 712 307;
Japanese Published Specifications Nos. 03 220 176, 02 207 083, 63 307 857, 63 287 764, 03 246 283, 04 9371, 03 279 359, 03 255 072, 05 178 833, 07 173 157, 08 291 171;
U.S. Pat. Nos. 5,034,524, 4,948,798, 4,918,086, 5,039,686, 5,034,404, 5,532,365, 4,849,432;
PCT Applications Nos. WO 91/17 659, 91/4965;
French Application No. 2 611 114;
Brazilian Application No. 88 03 621.

All the generic formulae and definitions described in these publications, and also the individual compounds described therein, are expressly incorporated herein by reference.

Some of these compounds are summarized under the term nitromethylenes, nitroimines and related compounds.

Preferably, these compounds can be summarized under the formula (III)

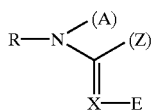
(III)

in which
R represents hydrogen or represents optionally substituted radicals selected from the group consisting of acyl, alkyl, aryl, aralkyl, heterocyclyl, heteroaryl or heteroarylalkyl;
A represents a monofunctional group selected from the group consisting of hydrogen, acyl, alkyl, aryl or represents a bifunctional group which is linked to the radical Z;
E represents an electron-withdrawing radical;
X represents the radicals —CH= or =N—, where the radical —CH= may be linked to the radical Z instead of an H atom;
Z represents a monofunctional group selected from the group consisting of alkyl, —O—R, —S—R,

where the radicals R are identical or different and are as defined above,
or represents a bifunctional group which is linked to the radical A or the radical X.

Particular preference is given to compounds of the formula (III) in which the radicals have the following meaning:
R represents hydrogen and represents optionally substituted radicals selected from the group consisting of acyl, alkyl, aryl, aralkyl, heterocyclylalkyl, heteroaryl, heteroarylalkyl.
Examples of acyl radicals are formyl, alkylcarbonyl, arylcarbonyl, alkylsulphonyl, arylsulphonyl, (alkyl-)-(aryl-)-phosphoryl, which may themselves be substituted.
Examples of alkyl are $C_1$–$C_{10}$-alkyl, in particular $C_1$–$C_4$-alkyl, specifically methyl, ethyl, i-propyl, sec- or t-butyl, which may themselves be substituted.
Examples of aryl are phenyl, naphthyl, in particular phenyl.
Examples of aralkyl are phenylmethyl, phenethyl.
An example of heterocyclylalkyl is the radical

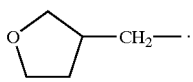

Examples of heteroaryl are heteroaryl having up to 10 ring atoms and N, O, S, in particular N, as heteroatoms. Specific examples are thienyl, furyl, thiazolyl, imidazolyl, pyridyl, benzothiazolyl, pyridazinyl.
Examples of heteroarylalkyl are heteroarylmethyl, heteroarylethyl having up to 6 ring atoms and N, O, S, in particular N, as heteroatoms, in particular optionally substituted heteroaryl as defined under heteroaryl.
Substituents which may be mentioned by way of example and by way of preference are:
alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, the halogen atoms being identical or different, and preferred halogen atoms being fluorine, chlorine or bromine, in particular fluorine, such as trifluoromethyl, hydroxyl; halogen, preferably fluorine, chlorine, bromine and iodine, in particular fluorine, chlorine and bromine, cyano; nitro; amino; monoalkyl- and dialkylamino having preferably 1 to 4, in particular 1 or 2, carbon atoms per alkyl group, such as methylamino, methylethylamino n- and i-propylamino and methyl-n-butylamino; carboxyl; carbalkoxy having preferably 2 to 4, in particular 2 or 3, carbon atoms, such as carbomethoxy and carboethoxy; sulpho ($SO_3H$); alkylsulphonyl having preferably 1 to 4, in particular 1 or 2, carbon atoms, such as methylsulphonyl and ethylsulphonyl; arylsulphonyl having preferably 6 or 10 arylcarbon atoms, such as phenylsulphonyl, and also heteroarylamino and heteroarylalkylamino such as chloropyridylamino and chloropyridylmethylamino.

A represents hydrogen or represents an optionally substituted radical selected from the group consisting of acyl, alkyl, aryl, which are preferably as defined under R, A furthermore represents a bifunctional group. Examples include optionally substituted alkylene having 1 to 4, in particular 1 to 2, C atoms, examples of substitutents being the substituents which have been mentioned further above (and where the alkylene groups may be interrupted by heteroatoms from the group consisting of N, O, S).

A and Z together with the atoms to which they are attached may form a saturated or unsaturated heterocyclic ring. The heterocyclic ring may contain a further 1 or 2 identical or different heteroatoms and/or heterogroups. Preferred heteroatoms are oxygen, sulphur or nitrogen, and preferred heterogroups are N-alkyl, where the alkyl of the N-alkyl group contains preferably 1 to 4, in particular 1 or 2, carbon atoms. Examples of alkyl include methyl, ethyl, n- and i-propyl and n-, i- and t-butyl. The heterocyclic ring contains 5 to 7, preferably 5 or 6 ring members.

Examples of compounds of the formula (III) in which R and Z together with the atoms to which they are attached form a ring include the following:

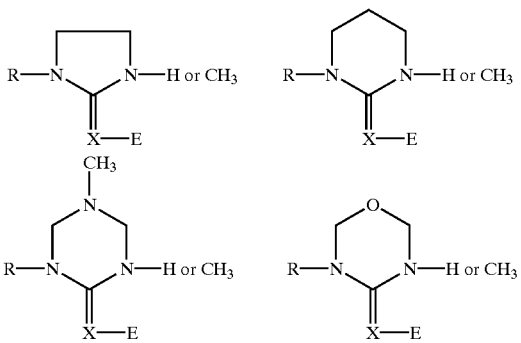

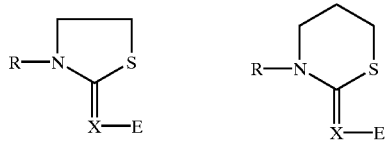

in which

E, R and X are each as defined above and further below.

E represents an electron-withdrawing radical, specific examples being NO₂, CN, halogenoalkylcarbonyl such as halogeno-C₁–C₄-alkylcarbonyl, for example COCF₃, alkylsulphonyl (for example SO₂–CH₃), halogenoalkylsulphonyl (for example SO₂CF₃) and with particular preference NO₂ or CN.

X represents —CH= or —N=.

Z represents an optionally substituted radical selected from the group consisting of alkyl, —OR, —SR, —NRR, where R and the substituents are preferably as defined above.

Z may, in addition to the ring mentioned above, together with the atom to which it is attached and the radical $$=\overset{|}{C}-$$

instead of X, form a saturated or unsaturated heterocyclic ring. The heterocyclic ring may contain a further 1 or 2 identical or different heteroatoms and/or heterogroups. Preferred heteroatoms are oxygen, sulphur or nitrogen and preferred heterogroups are N-alkyl, where the alkyl or N-alkyl group contains preferably 1 to 4, preferably 1 or 2, carbon atoms. Examples of alkyl include methyl, ethyl, n- and i-propyl and n-, i- and t-butyl. The heterocyclic ring contains 5 to 7, preferably 5 or 6, ring members. Examples of the heterocyclic ring include pyrrolidine, piperidine, piperazine, hexamethyleneimine, morpholine and N-methylpiperazine.

The agonists and antagonists of the nicotinic acetylcholine receptors are particularly preferably compounds of the formula (III) in which R represents

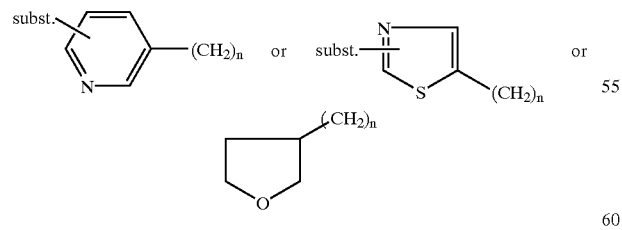

where n represents 0, 1 or 2, and preferably represents 1, subst. represents one of the substituents mentioned above, especially halogen, in particular chlorine, and A, Z, X and E are as defined above.

R represents in particular

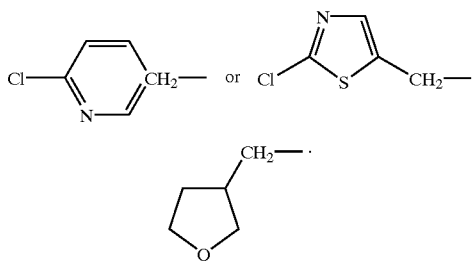

The following compounds are specific examples:

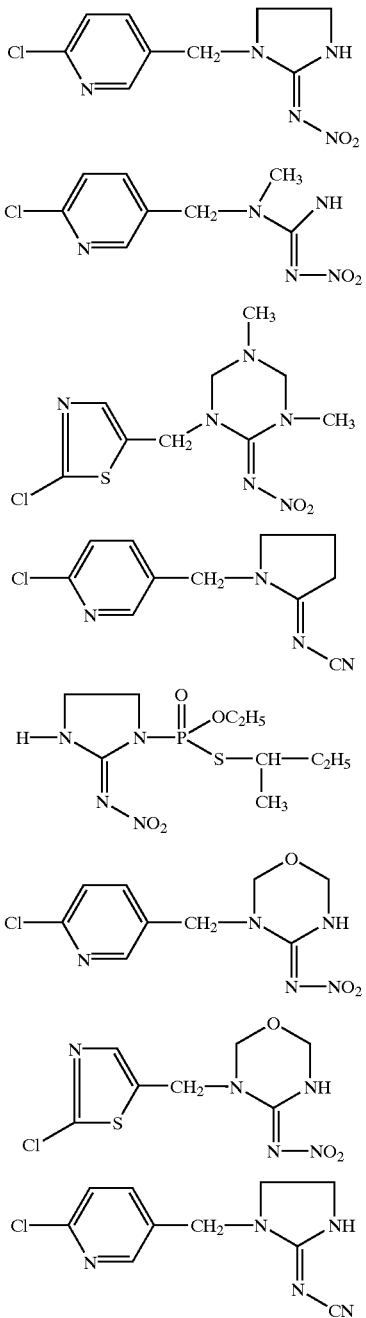

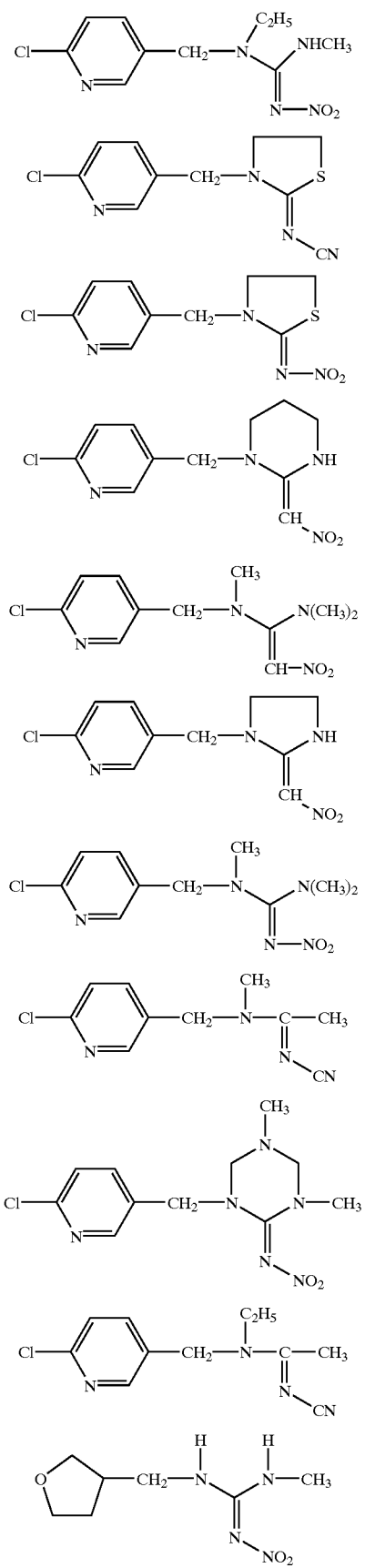
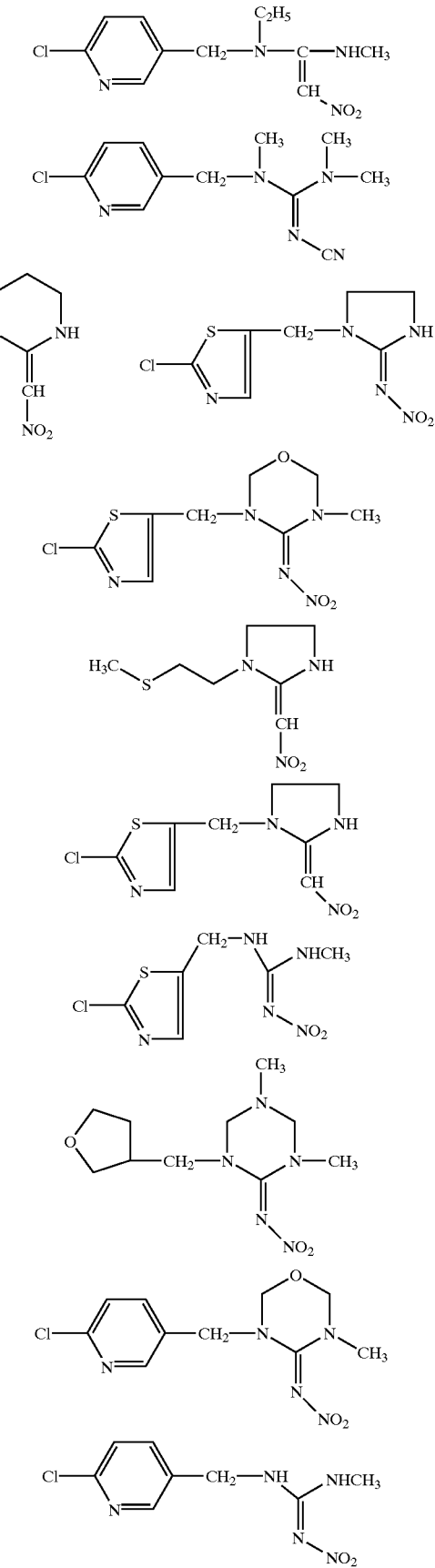

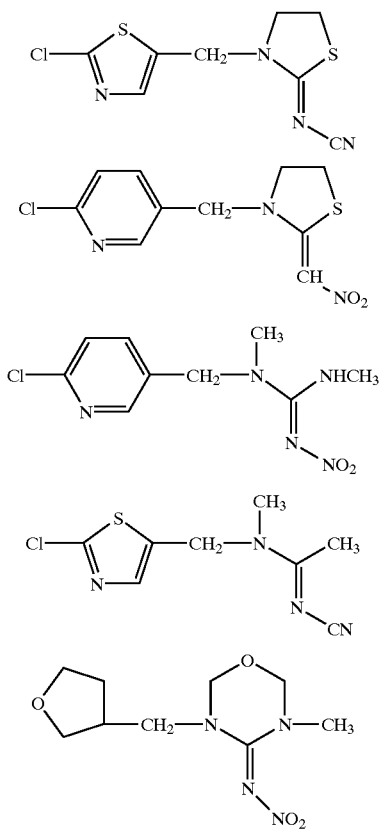
Very particularly preferred agonists and antagonists of the nicotinic acetylcholine receptors are compounds of the following formulae:
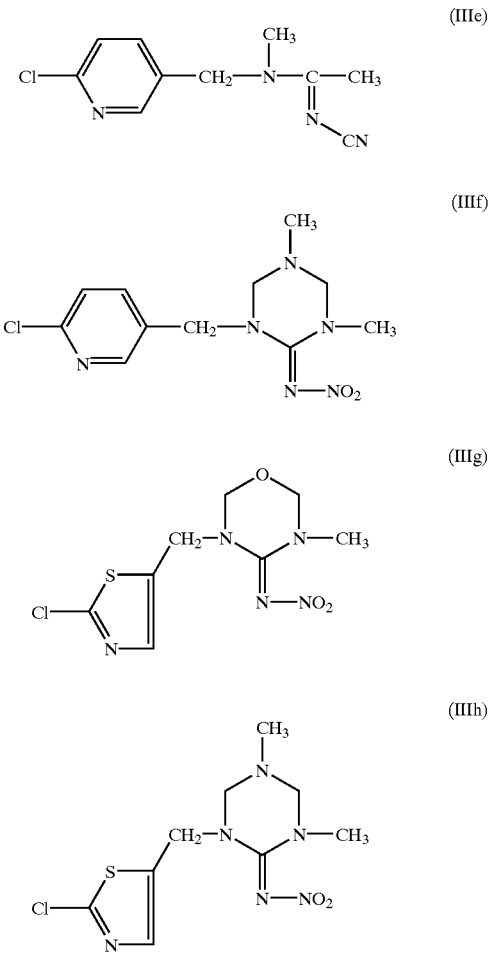
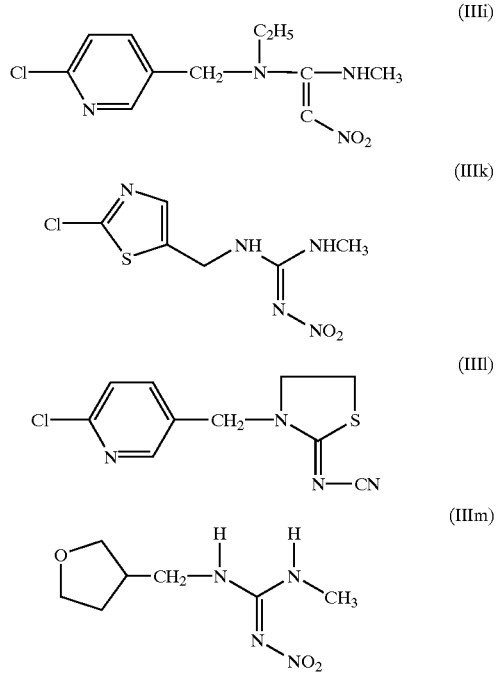

in particular a compound of the following formulae

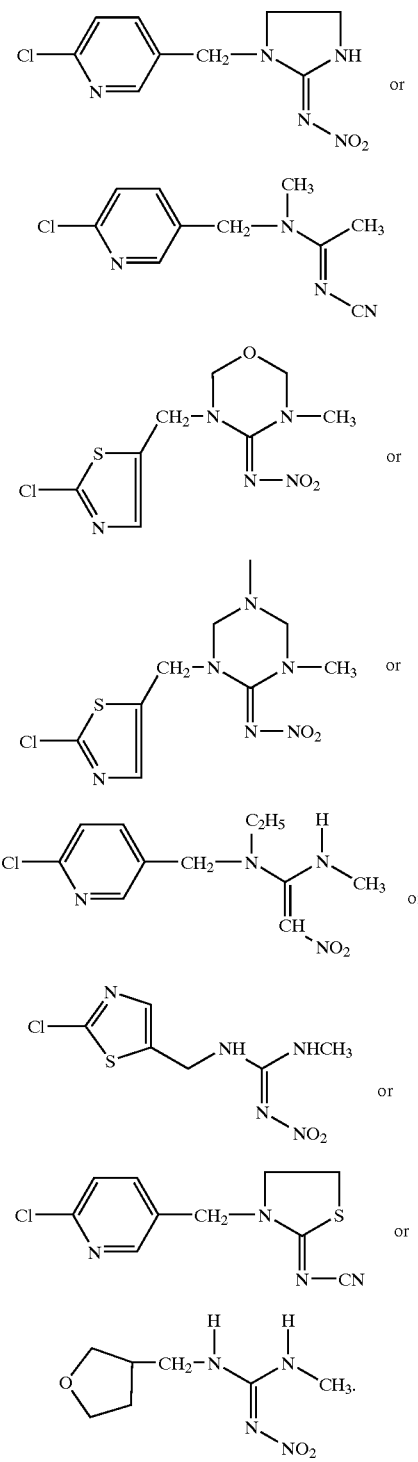

Very particular preference is given to the compounds of the formulae (IIIa), (IIIk), (IIIl).

Furthermore, very particular preference is given to the compounds of the formulae (IIIe), (IIIg), (IIIh), (IIIm), (IIIc).

The active compound mixtures are suitable for controlling animal pests, in particular insects, arachnids and nematodes, encountered in agriculture, in forests, in the protection of stored products and in the hygiene sector, and they are tolerated well by plants and have favourable toxicity to warm-blooded animals. They are active against normally sensitive and resistant species and against all or some stages of development. The abovementioned pests include:

From the order of the Isopoda, for example *Oniscus asellus, Armadillidium vulgare* and *Porcellio scaber.*

From the order of the Diplopoda, for example *Blaniulus guttulatus.*

From the order of the Chilopoda, for example *Geophilus carpophagus* and *Scutigera* spp.

From the order of the Symphyla, for example *Scutigerella immaculata.*

From the order of the Thysanura, for example *Lepisma saccharina.*

From the order of the Collembola, for example *Onychiurus armatus.*

From the order of the Orthoptera, for example *Acheta domesticus, Gryllotalpa* spp., *Locusta migratoria migratorioides, Melanoplus* spp. and *Schistocerca gregaria.*

From the order of the Blattaria, for example *Blatta orientalis, Periplaneta americana, Leucophaea maderae* and *Blattella germanica.*

From the order of the Dermaptera, for example *Forficula auricularia.*

From the order of the Isoptera, for example *Reticulitermes* spp.

From the order of the Phthiraptera, for example *Pediculus humanus corporis, Haematopinus* spp., *Linognathus* spp., *Trichodectes* spp. and *Damalinia* spp.

From the order of the Thysanoptera, for example *Hercinothrips femoralis, Thrips tabaci, Thrips palmi* and *Frankliniella accidentalis.*

From the order of the Heteroptera, for example *Eurygaster* spp., *Dysdercus intermedius, Piesma quadrata, Cimex lectularius, Rhodnius prolixus* and *Triatoma* spp.

From the order of the Homoptera, for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana* and *Cnaphalocerus* spp.

From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna*

*varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis* and *Costelytra zealandica*.

From the order of the Hymenoptera, for example *Diprion* spp., *Hoplocampa* spp., *Lasius* spp., *Monomorium pharaonis* and *Vespa* spp.

From the order of the Diptera, for example *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example *Xenopsylla cheopis* and *Ceratophyllus* spp.

From the class of arachnids, for example *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The synergistic effect is particularly pronounced if the active compounds in the active compound combinations are present at certain ratios by weight.

The ratio of the compounds of the formulae (I) and/or (II) employed and of the compound(s) of the formula (III), and the total amount of the mixture, depends on the type and the occurrence of the insects. For each application, the optimum ratios and total amounts to be employed can in each case be determined by test series. In general, the ratio of the compounds of the formulae (I) and/or (II) and the compound(s) of the formula (III) is from 1:100 to 100:1, preferably from 1:25 to 25:1 and particularly preferably from 1:5 to 5:1. These are parts by weight.

The active compound mixtures according to the invention can be present in their commercial formulations and in the use forms prepared from these formulations, in a mixture with other active compounds, such as insecticides, attractants, sterilants, acaricides, nematicides, fungicides, growth-regulating substances or herbicides. The insecticides include, for example, phosphoric esters, carbamates, carboxylic esters, chlorinated hydrocarbons, phenylureas, substances prepared by microorganisms. Specific co-components for mixtures are the insecticides and fungicides mentioned above.

Examples of insecticides which may optionally be admixed include:

phosphoric esters, such as azinphos-ethyl, azinphos-methyl, α-1(4-chlorophenyl)-4-(O-ethyl, S-propyl) phosphoryloxy-pyrazole, chlorpyrifos, coumaphos, demeton, demeton-S-methyl, diazinon, dichlorvos, dimethoate, ethoate, ethoprophos, etrimfos, fenitrothion, fenthion, heptenophas, parathion, parathion-methyl, phosalone, poxim, pirimiphos-ethyl, pirimiphos-methyl, profenofos, prothiofos, sullprofos, triazophos and trichlorphon;

carbamates, such as aldicarb, bendiocarb, α-2-(1-methylpropyl)-phenyl methyl-carbamate, butocarboxim, butoxycarboxim, carbaryl, carbofuran, carbosulfan, cloethocarb, isoprocarb, methomyl, oxamyl, pirimicarb, promecarb, propoxur and thiodicarb;

organosilicon compounds, preferably dimethyl(phenyl)silyl-methyl 3-phenoxybenzyl ethers, such as dimethyl-(4-ethoxyphenyl)-silylmethyl 3-phenoxybenzyl ether or (dimethylphenyl)-silyl-methyl 2-phenoxy-6-pyridylmethyl ethers such as, for example, dimethyl-(9-ethoxy-phenyl)-silylmethyl 2-phenoxy-6-pyridylmethyl ether or [(phenyl)-3-(3-phenoxyphenyl)-propyl [(dimethyl)-silanes such as, for example, (4-ethoxyphenyl)-[3-(4-fluoro-3-phenoxyphenyl-propyl] dimethyl-silane, silafluofen;

pyrethroids, such as allethrin, alphamethrin, bioresmethrin, byfenthrin, cycloprothrin, cyfluthrin, decamethrin, cyhalothrin, cypermethrin, deltamethrin, alpha-cyano-3-phenyl-2-methylbenzyl 2,2-dimethyl-3-(2-chloro-2-trifluoro-methylvinyl)cyclopropane-carboxylate, fenpropathrin, fenfluthrin, fenvalerate, flucythrinate, flumethrin, fluvalinate, permethrin, resmethrin and tralomethrin;

nitroimines and nitromethylenes, such as 1-[(6-chloro-3-pyridinyl)-methyl]-4,5-dihydro-N-nitro-1H-imidazole-2-amine (imidacloprid), N-[(6-chloro-3-pyridyl)-methyl]-$N^2$-cyano-$N^1$-methylacetamide (NI-25);

abamectin, AC 303, 630, acephate, acrinathrin, alanycarb, aldoxycarb, aldrin, amitraz, azamethiphos, *Bacillus thuringiensis*, phosmet, phosphamidon, phosphine, prallethrin, propaphos, propetamphos, prothoate, pyraclofos, pyrethrins, pyridaben, pyridafenthion, pyriproxyfen, quinalphos, RH-7988, rotenone, sodium fluoride, sodium hexafluorosilicate, sulfotep, sulfuryl fluoride, tar oils, teflubenzuron, tefluthrin, temephos, terbufos, tetrachlorvinphos, tetramethrin, O-2-tert-butyl-pyrimidin-5-yl-o-isopropyl-phosphorothiate, thiocyclam, thiofanox, thiometon, tralomethrin, triflumuron, trimethacarb, vamidothion, *Verticillium Lacanii*, XMC, xylylcarb, benfuracarb, bensultap, bifenthrin, bioallethrin, MERbioallethrin (S)-cyclopentenyl isomer, bromophos, bromophos-ethyl, buprofezin, cadusafos, calcium polysulphide, carbophenothion, cartap, quinomethionate, chlordane, chlorfenvinphos, chlorfluazuron, chlormephos, chloropicrin, chlorpyrifos, cyanophos, beta-cyfluthrin, alpha-cypermethrin, cyophenothrin, cyromazine, dazomet, DDT, demeton-S-methylsulphone, diafenthiuron, dialifos, dicrotophos, diflubenzuron, dinoseb, deoxabenzofos, diazacarb, disulfoton, DNOC, empenthrin, endosulfan, EPN, esfenvalerate, ethiofencarb, ethion, etofenprox, fenobucarb, fenoxycarb, fensulfothion, fipronil, flucycloxuron, flufenprox, flufenoxuron, fonofos, formetanate, fornothion, fosmethilan, furathiocarb, heptachlor, hexaflumuron, hydramethylnon, hydrogen cyanide, hydroprene, IPSP, isazofos, isofenphos, isoprothiolane, isoxathion, iodfenphos, kadethrin, lindane, malathion, mecarbam, mephosfolan, mercurous chloride, metam, metarthizium, anisopliae, methacrifos, methamidophos, methidathion, methiocarb, methoprene, methoxychlor, methyl isothiocyanate, metolcarb, mevinphos, monocrotophos, naled, Neodiprion sertifer NPV, nicotine, omethoate, oxydemeton-methyl, pentachlorophenol, petroleum oils, phenothrin, phenthoate, phorate.

The other insecticides that may optionally be admixed may also be from the class of the compounds of the general formula (I).

Fungicides which may optionally be admixed are preferably:

Triazoles such as:

azaconazole, propiconazole, tebuconazole, cyproconazole, metconazole, amitrole, azocyclotin, BAS 480F, bitertanol, difenoconazole, fenbuconazole, fenchlorazole, fenethanil, fluquinconazole, flusilazole, flutriafol, imibenconazole, isozofos, myclobutanil, paclobutrazol, (±)-cis-1-(4-chlorophenyl)-2-(1H-1,2,4-triazol-1-yl)-cycloheptanol, tetraconazole, triadimefon, triadimenol, triapenthenol, triflumizole, triticonazole, uniconazole and their metal salts and acid adducts.

Imidazoles such as:

imazalil, pefurazoate, prochloraz, triflumizole, 2-(1-tert-butyl)-1-(2-chlorophenyl)-3-(1,2,4-triazol-1-yl)-propan-2-ol, thiazolecarboxanilides such as 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one and their metal salts and acid adducts.

Methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-methylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluorophenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[2-[(3-methyl-pyridin-2-yloxymethyl)phenyl]-3-methoxyacrylate, methyl (E)-2-[2-[6-(2-methyl-phenoxy)pyrimidin-4-yloxy] phenyl]-3-methoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-acrylate, methyl (E),(E)-2-{ 2-(3-methoxyphenyl)methyloximinomethyl]-phenyl}-3-methoxyacrylate, methyl (E)-2-{2-(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate;

Succinate dehydrogenase inhibitors such as:

fenfuram, furcarbanil, cyclafluramid, furmecyclox, seedvax, metsulfovax, pyrocarbolid, oxycarboxin, shirlan, mebenil (mepronil), benodanil, flutolanil (Moncut);

naphthalene derivatives such as terbinafine, naftifine, butenafine, 3-chloro-7-(2-aza-2,7,7-trimethyl-oct-3-en-5-ine);

sulphenamides such as dichlofluanid, tolylfluanid, folpet, fluorfolpet; captan, captofol;

benzimidazoles such as carbendazim, benomyl, furathiocarb, fuberidazole, thiophonatmethyl, thiabendazole or their salts;

morpholine derivatives such as fenpropimorph, falimorph, dimethomorph, dodemorph, aldimorph, fenpropidine and their arylsulphonates, such as, for example, p-toluenesulphonic acid and p-dodecylphenyl-sulphonic acid;

dithiocarbamates, cufraneb, ferbam, mancopper, mancozeb, maneb, metam, metiram, thiram zeneb, ziram:

benzothiazoles, such as 2-mercaptobenzothiazole;

benzamides, such as 2,6-dichloro-N-(4-trifluoromethylbenzyl)-benzamide;

boron compounds, such as boric acid, boric esters, borax;

formaldehyde and formaldehyde-releasing compounds, such as benzyl alcohol mono-(poly)-hemiformal, oxazolidine, hexa-hydro-S-triazines, N-methylolchloroacetamide, paraformaldehyde, nitropyrin, oxolinic acid, tecloftalam;

tris-N-(cyclohexyldiazeniumdioxy)-aluminium, N-(cyclo-hexyldiazeniumdioxy)-tri-butyltin or K salts, bis-N-(cyclohexyldiazeniumdioxy)-copper, N-methylisothiazolin-3-one, 5-chloro-N-methylisothiazolin-3-one, 4,5-dichloro-N-octylisothiazolin-3-one, N-octyl-isothiazolin-3-one, 4,5-trimethylene-isothiazolinone, 4,5-benzoisothiazolinone, N-methylolchloroacetamide;

aldehydes, such as cinnamaldehyde, formaldehyde, glutaraldehyde, β-bromo-cinnamaldehyde;

thiocyanates, such as thiocyanatomethylthiobenzothiazole, methylenebisthiocyanate, and the like;

quaternary ammonium compounds, such as benzyldimethyltetradecylammonium chloride, benzyldimethyldodecylammonium chloride, didecyldimethylammonium chloride;

iodine derivatives, such as diiodomethyl p-tolyl sulphone, 3-iodo-2-propinyl alcohol, 4-chlorophenyl-3- iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate;

phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol and their alkali metal and alkaline earth metal salts;

microbicides having an activated halogen group, such as chloroacetamide, bronopol, bronidox, tectamer, such as 2-bromo-2-nitro-1,3-propanediol, 2-bromo-4'-hydroxy-acetophenone, 2,2-dibromo-3-nitrile-propionamide, 1,2-dibromo-2,4-dicyanobutane, β-bromo-β-nitrostyrene;

pyridines, such as 1-hydroxy-2-pyridinethione (and their Na, Fe, Mn, Zn salts), tetrachloro-4-methylsulphonylpyridine, pyrimethanol, mepanipyrim, dipyrithion, 1-hydroxy-4-methyl-6-(2,4,4-trimethylpentyl)-2(1H)-pyridine;

metal soaps, such as tin naphthenate, copper naphthenate, zinc naphthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate and zinc benzoate;

metal salts, such as copper hydroxycarbonate, sodium dichromate, potassium dichromate, potassium chromate, copper sulphate, copper chloride, copper borate, zinc fluorosilicate, copper fluorosilicate, in particular mixtures with fixatives;

oxides, such as tributyltin oxide, $Cu_2O$, CuO, ZnO;

dialkyldithiocarbamates, such as Na and Zn salts of dialkyldithiocarbamates, tetramethylthiuram disulphide, potassium N-methyl-dithiocarbamate;

nitriles, such as 2,4,5,6-tetrachloroisophthalodinitrile, disodium cyano-dithioimido-carbamate;

quinolines, such as 8-hydroxyquinoline, and their Cu salts;

mucochloric acid, 5-hydroxy-2(5H)-furanone;

4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, potassium N-hydroxy-methyl-N'-methyl-dithiocarbamate, 2-oxo-2-(4-hydroxy-phenyl)acetohydroximic acid chloride, phenyl-(2-chloro-cyano-vinyl)sulphone, phenyl-(1,2-dichloro-2-cyano-vinyl)sulphone;

Ag-, Zn- or Cu-containing zeolites, alone or enclosed in polymeric active compounds, or else mixtures of more than one of the abovementioned fungicides.

The active compound content of the use forms prepared from the commercial formulations can vary within wide limits. The active compound concentration of the use forms can be from 0.0000001 to 95% by weight of active compound, preferably between 0.0001 and 1% by weight.

The mixtures of active compounds can be converted into the customary formulations, such as solutions, emulsions, suspensions, powders, foams, pastes, granules, aerosols, active-compound-impregnated natural and synthetic materials, very fine encapsulations in polymeric substances and in coating compositions for seed, furthermore in formulations with smokes, such as fumigating cartridges, fumigating cans, fumigating coils and the like, and also ULV cold fogging and warm mist formulations.

These formulations are prepared in a known manner, for example by mixing the active compounds with extenders, that is, liquid solvents, pressurized liquefied gases and/or solid carriers, optionally with the use of surfactants, that is, emulsifiers and/or dispersants, and/or foam-forming agents. If the extender used is water, it is also possible to use, for example, organic solvents as auxiliary solvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol and also their ethers and esters, ketones, such as acetone, methyl ethyl ketone, methyl isobutyl ketone or cyclohexanone, strongly polar solvents, such as dimethylformamide and dimethyl sulphoxide, and also water; by liquefied gaseous extenders or carriers are meant liquids which are gaseous at ambient temperature and under atmospheric pressure, for example aerosol propellant, such as halogenated hydrocarbons and also butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifiers and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersing agents are: for example lignin-sulphite waste liquors and methylcellulose.

Tackifiers such as carboxy-methylcellulose and natural and synthetic polymers in the form of powders, granules or latices, such as gum arabic, polyvinyl alcohol and polyvinyl acetate, and also natural phospholipids, such as cephalins and lecithins, and synthetic phospholipids, can be used in the formulations. Further additives may be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 percent by weight of active compound mixture, preferably between 0.5 and 90 percent by weight of active compound mixture.

The mixtures according to the invention can be applied via the soil.

The mixtures according to the invention can be applied via the leaf.

The mixtures according to the invention can be employed particularly advantageously for seed dressing.

Furthermore, the mixtures according to the invention can preferably be applied via the soil.

Furthermore, it is also possible to apply the mixtures according to the invention via an irrigation system, for example via the water for irrigation.

Furthermore, it has been found that it is also possible to apply the active components of the mixtures according to the invention separately, for example, to apply the spinosyn(s), advantageously in the form of a suitable formulation, onto the soil, and to use the compound or the compounds of the formula (III), advantageously in the form of a suitable formulation, via the leaf, or vice versa.

USE EXAMPLES

Example 1

Activity Of Folia-Insecticidal Formulations Against Sucking Pests

The insecticidal activity was examined using the critical concentration test. From each of the test preparations, an aqueous dilution series is made by diluting the individual concentrations by the factor 5.

To determine any synergistic activity, weakly active concentrations of chloronicotinyl compounds are combined with various active compound concentrations of Tracer (Spinosad).

The test plants used are cabbage plants at the one-leaf stage which are infested by *Myzus persicae* (green peach aphid). The shoots or leaves with the aphids are dipped for approximately 3 seconds into the respective liquors. The experiments are subsequently placed in a greenhouse at 21° C. and 65% relative atmospheric humidity.

Evaluation for mortality is carried out after 2 and 7 days.

TABLE 1

| Mixtures of compound (IIIa) and Spinosad | | | | | | |
|---|---|---|---|---|---|---|
| Act. | Myzus persicae on cabbage/kill in % Evaluation after | | | | | |
| compd. | 2 days | | | 7 days | | |
| conc. (% a.i.) Spinosad | Spinosad | Compound (IIIa) 0.0008% a.i. | Spinosad & compound (IIIa) | Spinosad | Compound (IIIa) 0.0008% a.i. | Spinosad & compound (IIIa) |
| 0.1 | 0 | 90 | 100 | 0 | 78 | 100 |
| 0.02 | 0 | 90 | 100 | 0 | 78 | 100 |
| 0.004 | 0 | 90 | 100 | 0 | 78 | 100 |
| 0.0008 | 0 | 90 | 97 | 0 | 78 | 92 |
| 0.00016 | 0 | 90 | 95 | 0 | 78 | 86 |
| Spinosad | Spinosad | Compound (IIIa) 0.00016% a.i. | Spinosad & compound (IIIa) | Spinosad | Compound (IIIa) 0.00016% a.i. | Spinosad & compound (IIIa) |
| 0.1 | 0 | 18 | 95 | 0 | 2 | 99 |
| 0.02 | 0 | 18 | 89 | 0 | 2 | 99 |
| 0.004 | 0 | 18 | 86 | 0 | 2 | 80 |
| 0.0008 | 0 | 18 | 56 | 0 | 2 | 33 |
| 0.00016 | 0 | 18 | 19 | 0 | 2 | 3 |
| Control | | | 0 | | | 0 |

Act. compd. conc. = active compound concentration
a.i. = active ingredient

TABLE 2

| Mixtures of compound (IIIg) and Spinosad | | | | | | |
|---|---|---|---|---|---|---|
| Act. | Myzus persicae on cabbage/kill in % Evaluation after | | | | | |
| compd. | 2 days | | | 7 days | | |
| conc. (% a.i.) Spinosad | Spinosad | Compound (IIIg) 0.0008% a.i. | Spinosad & compound (IIIg) | Spinosad | Compound (IIIg) 0.0008% a.i. | Spinosad & compound (IIIg) |
| 0.1 | 0 | 79 | 100 | 0 | 70 | 100 |
| 0.02 | 0 | 79 | 100 | 0 | 70 | 100 |
| 0.004 | 0 | 79 | 96 | 0 | 70 | 98 |
| 0.0008 | 0 | 79 | 90 | 0 | 70 | 91 |

TABLE 2-continued Mixtures of compound (IIIg) and Spinosad

| Spinosad | Spinosad | Compound (IIIg) 0.00016% a.i. | Spinosad & compound (IIIg) | Spinosad | Compound (IIIg) 0.00016% a.i. | Spinosad & compound (IIIg) |
|---|---|---|---|---|---|---|
| 0.1 | 0 | 0 | 87 | 0 | 0 | 77 |
| 0.02 | 0 | 0 | 85 | 0 | 0 | 98 |
| 0.004 | 0 | 0 | 63 | 0 | 0 | 33 |
| Control | | | 0 | | | 0 |

Act. compd. conc. = active compound concentration
a.i. = active ingredient

TABLE 3

Mixtures of compound (IIIk) and Spinosad

| | Myzus persicae on cabbage/kill in % Evaluation after | | | | | |
|---|---|---|---|---|---|---|
| Act. compd. conc. (% a.i.) | 2 days | | | 7 days | | |
| Spinosad | Spinosad | Compound (IIIk) 0.0008% a.i. | Spinosad & compound (IIIk) | Spinosad | Compound (IIIk) 0.0008% a.i. | Spinosad & compound (IIIk) |
| 0.1 | 0 | 48 | 100 | 0 | 28 | 100 |
| 0.02 | 0 | 48 | 100 | 0 | 28 | 100 |
| 0.004 | 0 | 48 | 98 | 0 | 28 | 100 |
| 0.0008 | 0 | 48 | 97 | 0 | 28 | 99 |
| 0.00016 | 0 | 48 | 90 | 0 | 28 | 82 |

| Spinosad | Spinosad | Compound (IIIk) 0.00016% a.i. | Spinosad & compound (IIIk) | Spinosad | Compound (IIIk) 0.00016% a.i. | Spinosad & compound (IIIk) |
|---|---|---|---|---|---|---|
| 0.1 | 0 | 10 | 95 | 0 | 2 | 98 |
| 0.02 | 0 | 10 | 97 | 0 | 2 | 54 |
| 0.004 | 0 | 10 | 84 | 0 | 2 | 55 |
| 0.0008 | 0 | 10 | 35 | 0 | 2 | 27 |
| Control | | | 0 | | | 0 |

Act. compd. conc. = active compound concentration
a.i. = active ingredient

TABLE 4

Mixtures of compound (III 1) and Spinosad

| | Myzus persicae on cabbage/kill in % Evaluation after | | | | | |
|---|---|---|---|---|---|---|
| Act. compd. conc. (% a.i.) | 2 days | | | 7 days | | |
| Spinosad | Spinosad | Compound (III 1) 0.0008% a.i. | Spinosad & compound (III 1) | Spinosad | Compound (III 1) 0.0008% a.i. | Spinosad & compound (III 1) |
| 0.1 | 0 | 85 | 100 | 0 | 38 | 100 |
| 0.02 | 0 | 85 | 100 | 0 | 38 | 99 |
| 0.004 | 0 | 85 | 100 | 0 | 38 | 83 |
| 0.0008 | 0 | 85 | 93 | 0 | 38 | 95 |
| 0.00016 | 0 | 85 | 83 | 0 | 38 | 53 |

| Spinosad | Spinosad | Compound (III 1) 0.00016% a.i. | Spinosad & compound (III 1) | Spinosad | Compound (III 1) 0.00016% a.i. | Spinosad & compound (III 1) |
|---|---|---|---|---|---|---|
| 0.1 | 0 | 8 | 94 | 0 | 0 | 94 |
| 0.02 | 0 | 8 | 94 | 0 | 0 | 82 |
| 0.004 | 0 | 8 | 93 | 0 | 0 | 54 |
| 0.0008 | 0 | 8 | 53 | 0 | 0 | 20 |

TABLE 4-continued

| Mixtures of compound (III 1) and Spinosad | | | | | | |
|---|---|---|---|---|---|---|
| 0.00016 | 0 | 8 | 22 | 0 | 0 | 2 |
| Control | | | 0 | | | 0 |

Act. compd. conc. = active compound concentration
a.i. = active ingredient

Example 2

Critical Concentration Test/Root-Systemic Action

| | |
|---|---|
| Test insect: | Aphis fabae |
| Solvent: | 4 parts by weight of acetone |
| Emulsifier: | 1 part by weight of alkylaryl polyglycol ether |

To produce a suitable preparation of active compound, 1 part by weight of active compound is mixed with a stated amount of solvent, the stated amount of emulsifier is added and the concentrate is diluted with water to the desired concentration.

The active compound preparation is mixed intimately with soil. The concentration of the active compound in the preparation is of virtually no importance, only the amount by weight of active compound per unit volume of soil, which is given in ppm (=mg/l), being decisive. The treated soil is filled into 250 ml pots and the pots are planted with pre-germinated broad beans. In this manner, the active compound can be taken up from the soil by the roots of the plants and transported into the leaves.

To demonstrate the root-systemic effect, the leaves are populated with the abovementioned test animals after 7 days. After a further 7 days, the test is evaluated by estimating the dead animals. The root-systemic effect of the active compound is deduced from the destruction figures. It is 100% when all the test animals have been killed and 0% when just as many test insects are still alive as in the untreated control.

Active compounds, application rates and results are shown in the table below:

TABLE

Root-systemic
Aphis fabae

| Active compound | | Degree of destruction in % at active compound concentrations |
|---|---|---|
| According to the invention | Spinosad | 40 ppm = 0% |
| | compound (IIIa) | 0.035 ppm = 50% |
| | Spinosad + compound (IIIa) | 40 ppm + 0.035 ppm = 80% |

Example 3

Critical Concentration Test/Root-Systemic Action

| | |
|---|---|
| Test insect: | Phaedon cochleariae larvae |
| Solvent: | 4 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The active compound preparation is mixed intimately with soil. The concentration of the active compound in the preparation is of virtually no importance, only the amount by weight of active compound per unit volume of soil, which is given in ppm (=mg/l), being decisive. The treated soil is filled into 500 ml pots, 8 cabbage seeds are placed at a depth of approximately 1 cm, the hole is filled and the soil surface is pressed down gently.

To demonstrate the root-systemic effect, the leaves are populated with the abovementioned test animals after 9 days. After a further 3 days, the test is evaluated by estimating the leaf-feeding in the treated and in the untreated plant. The effect is 100% if, compared with the untreated control, only little feeding damage is observed; it is 0% when the entire cabbage has been eaten.

Active compounds, application rates and results are shown in the table below.

TABLE

Root-systemic
Phaedon cochleariae larvae

| | Active compound | Degree of destruction in % at active compound concentrations |
|---|---|---|
| According to the invention: | Compound (III 1) | 2.50 ppm = 0% |
| | Spinosad + compound (III 1) | 2.50 ppm + 2.50 ppm = 90% |
| According to the invention: | Compound (IIIe) | 5.00 ppm = 0% |
| | Spinosad + compound (IIIe) | 2.50 ppm + 5.00 ppm = 98% |
| According to the invention: | Compound (IIIa) | 1.25 ppm = 0% |
| | Spinosad + compound (IIIa) | 2.50 ppm + 1.25 ppm = 80% |
| According to the invention: | Compound (IIIk) | 0.30 ppm = 0% |
| | Spinosad + compound (IIIk) | 2.50 ppm + 0.30 ppm = 80% |
| According to the invention: | Compound (IIIg) | 0.30 ppm = 50% |
| | Spinosad + compound (IIIg) | 2.50 ppm + 0.30 ppm = 80% |

What is claimed is:

1. A composition for controlling animal pests, consisting essentially of a synergistically effective mixture of one or more spinosyns and at least one agonist or antagonist of nicotinic acetylcholine receptors except for those of the formula (III) below

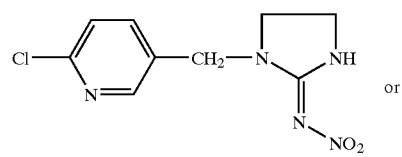

(IIIa)

or

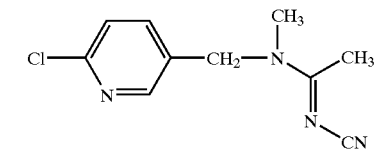 (IIIe)

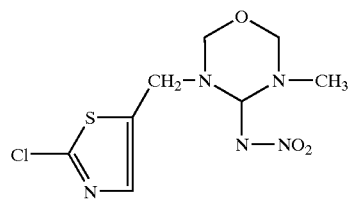 (IIIg)

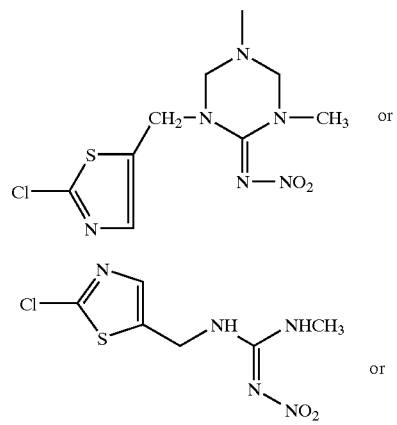 (IIIh)

or

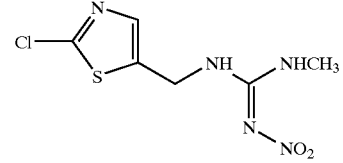 (IIIk)

or

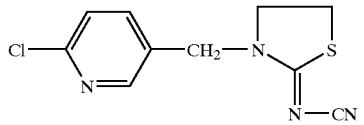 (III l)

or

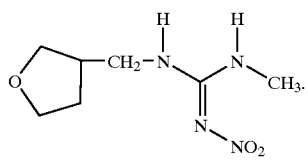 (IIIm)

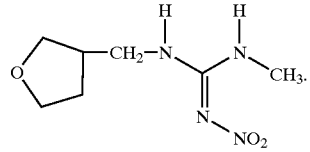 (IIIm)

2. The composition of claim 1, wherein the one or more spinosyns and at least one agonist or antagonist of nicotinic acetylcholine receptors are present in a ratio of from 1:100 to 100:1.

3. A process for preparing a pesticide consisting essentially of mixing a synergistically effective mixture of the one or more spinosyns and at least one agonist or antagonist of nicotinic acetylcholine receptors of claim 1 with at least one of extenders and surfactants.

4. A method of controlling at least one of an insect, an arachnid or a nematode comprising applying a synergistically effective mixture of the one or more spinosyns and at least one agonist or antagonist of nicotinic acetylcholine receptors of claim 1 to said insect, arachnid or nematode and/or its habitat.

* * * * *